United States Patent
Braun et al.

(10) Patent No.: US 6,719,834 B1
(45) Date of Patent: Apr. 13, 2004

(54) POLYELECTROLYTE CEMENT (75) Inventors: Peter Braun, Penzing (DE); Jürgen Glaser, Steinebach (DE); Hermann Nirschl, Seefeld (DE); Klaus-Peter Stefan, Seefeld (DE)

(73) Assignee: 3M ESPE AG, Seefeld (DE)

( * ) Notice: Subject to any disclaimer, the term of this patent is extended or adjusted under 35 U.S.C. 154(b) by 0 days.

(21) Appl. No.: 09/937,841

(22) PCT Filed: Mar. 31, 2000

(86) PCT No.: PCT/EP00/02855

§ 371 (c)(1),
(2), (4) Date: Sep. 28, 2001

(87) PCT Pub. No.: WO00/59452

PCT Pub. Date: Oct. 12, 2000

(30) Foreign Application Priority Data

Apr. 1, 1999 (DE) .......................... 199 14 975

(51) Int. Cl.$^7$ ................................. C09K 3/00
(52) U.S. Cl. .................. 106/35; 523/116; 433/226; 433/228.1; 428/407; 206/219; 206/222; 206/277; 222/95; 222/630
(58) Field of Search ................. 106/35; 523/116; 433/226, 228.1; 428/407; 222/251, 95, 630; 206/219, 222, 277

(56) References Cited

U.S. PATENT DOCUMENTS 5,512,611 A * 4/1996 Mitra .................... 523/116

FOREIGN PATENT DOCUMENTS

| DE | 3610844 | 10/1986 |
|----|---------|---------|
| DE | 3610845 | 10/1986 |
| DE | 3925306 | 2/1990 |
| DE | 3946329 | 6/1990 |
| DE | 4019617 | 1/1992 |
| DE | 4104934 | 8/1992 |
| DE | 4124441 | 1/1993 |
| DE | 19526224 | 1/1996 |
| DE | 4433811 | 3/1996 |
| DE | 19605272 | 8/1996 |
| DE | 19906834 | 8/1999 |
| EP | 0219058 | 4/1987 |
| GB | 2173184 | 10/1986 |
| GB | 2173207 | 10/1986 |
| WO | 9221632 | 12/1992 |

OTHER PUBLICATIONS

Masashi, et al.: Chemical Abstract vol. 126, Ref. 190912 (1996).

* cited by examiner

Primary Examiner—Paul Marcantoni
(74) Attorney, Agent, or Firm—Birch, Stewart, Kolasch & Birch, LLP (57) ABSTRACT

The invention relates to a single-component or multiple-component polyelectrolyte cement containing at least two reaction partners:

(a) at least one metal-cation-releasing compound and
(b) one or more polyelectrolytes capable of being converted into a solid state, wherein at least one of the polyelectrolytes is at least partially water soluble, and wherein at least a part of the reaction partner (a) and/or (b) is coated with an organic surface-coating agent.

In one preferred embodiment, at least one part of the formulation constituents of the cement is present in granulated form, wherein at least a part of the reaction partner (b) serves as an essential granulation agent. The polyelectrolyte cement is particularly stable in storage and can be easily mixed.

14 Claims, 2 Drawing Sheets

POLYELECTROLYTE CEMENT

This application is the national phase under 35 U.S.C. §371 of PCT International Application No. PCT/EP00/02855 which has an International filing date of Mar. 31, 2000, which designated the United States of America and was not published in English.

The invention relates to a single-component or multiple-component polyelectrolyte cement containing at least two reaction partners, (a) a metal-cation-releasing compound and (b) one or more polyelectrolytes capable of being converted into a solid state, wherein at least one of the polyelectrolytes is at least partially water soluble, and wherein at least one part of reaction partner (a) and/or (b) is coated with an organic surface coating agent. Moreover, the invention relates to a granulate obtained from at least one part of the formulation constituents of the polyelectrolyte cement present in solid form, wherein, in the context of an autogenous granulation process, at least one part of reaction partner (b) serves as the essential granulation agent, and the granulate disintegrates back to the primary grain on contact with the liquid formulation constituents.

Furthermore, the invention relates to processes for production of the granulate and the use of the polyelectrolyte cement as a dental material.

In the sense of the present invention, polyelectrolytes are understood to be polymers with ionically dissociable groups, which may be a component or a substituent of the polymer chain and of which the number is so great that the polymers are at least partially water soluble at least in their partially dissociated form. In the sense of the present invention, polyelectrolyte cements are understood to be materials which contain a polyelectrolyte. In particular, these polyelectrolytes should be able to react with a metal-ion-releasing compound in the context of a chelate-forming reaction, particularly preferably, an acid-base reaction/neutralization reaction. This reaction is described as a curing reaction or simply as curing. A polymerization reaction may also take place alongside this curing, if polymerizable compounds are added together with initiators suitable for the polymerization of these compounds.

Polyelectrolyte cements of this kind are obtained, for example, through the reaction of a polyalkenoic acid, in particular a polyacrylic acid, with zinc oxide or a metal-cation-releasing, so-called basic glass powder in the presence of water. These cements have been known since 1967 as polycarboxylic cements [D. C. Smith, Biomaterials 19, 467–478 (1998)] and since 1969 as (conventional) glass-ionomer cements (glass-polyalkenoate cements, GIC) [A. D. Wilson, B. E. Kent, DE 20 61 513]. Polyelectrolyte cements which contain additional polymerizable compounds and suitable initiators are, for example, synthetically modified glass-ionomer cements (see e.g. R. Mathis, I. L. Ferracane, J. Dent. Res. 66, 113 (Abstract 51) (1987)] or compomers [see e.g. EP 219 058].

The above named polyelectrolyte cements can be formulated as two-component paste-paste systems and single-component paste systems. Normally, however, the above-named polyelectrolyte cements are formulated as powder-liquid systems. In this context, the polyelectrolyte may be either in the liquid, or it may be mixed with the powder as a solid. Mixed forms, in which parts of the polyelectrolyte are contained in the powder and parts in the liquid, are also known [see, for example, GB-A-17880-72, DE-A-2319715]. Solid mixtures, in which at least one part of the polyelectrolyte is present alongside a metal-cation-releasing compound, are defined as "dry powder mixtures".

Addition of polyelectrolytes to the powder as a solid is advantageous, for example, if additional processing time is to be gained by the dissolution of the polyelectrolyte or if the complete amount of polyelectrolyte in the solution leads to a high, and therefore no longer suitable viscosity and workability.

One disadvantage of the dry powder mixture is that in the presence of moisture, e.g. from atmospheric humidity during the storage of the product up to the time of use, a reaction takes place between the two reaction partners, i.e. the metal-cation-releasing compound and the polyelectrolyte, which slows down the curing of the cement. This means that a reliable use of the polyelectrolyte cement is no longer guaranteed, because the curing of the material increases in dependence upon the duration of storage.

This plays an important role, in particular with the hand-mixed variants of these polyelectrolyte cements, because these products are conceived for the cost-conscious user in such a manner that several applications can be implemented with the packaged material. Accordingly, the dry powder mixture is provided in small glass containers which allow access to atmospheric moisture every time the material is removed, which slows down the curing. Moreover, in time, it becomes more difficult to mix the cement because, as a result of the reaction occurring at the surface between the metal-cation-releasing compound and the polyelectrolyte in the presence of atmospheric humidity, agglomerates of increased solidity may be formed and can only be broken down with an increased input of energy during mixing.

It is possible to achieve stable curing throughout the storage period by preventing the access of moisture to the dry powder mixture. This can only be realized through more elaborate packaging: for example, polyelectrolyte cements of this kind which are offered in a mixing capsule specially developed for single application, are blister-packed in aluminium foil possibly with an additional dessicant pad. Indeed, this measure does have the desired stabilizing effect on curing, but is associated with significantly increased cost of manufacture which is therefore transferred to the consumer. Moreover, with increasing awareness of environmental matters, the consumer's acceptance of an elaborately packaged product is constantly declining.

Also, particular steps must be taken during production and packaging of the dry powder mixture in order to minimize contact with atmospheric moisture as much as possible, otherwise initial damage to the dry powder mixture may occur and this may cause difficulties with the packaging of the dry powder mixture which leads to increased expenditure on maintenance.

Another option for protecting substances essentially from environmental influences is to provide the substances to be protected with a coating.

Organic coating compounds used in the production of tablets [H. P. Fiedler, Lexicon der Hilfsstoffe für Pharmazie, Kosmetik und angrenzende Gebiete (Dictionary of excipients for pharmaceutical, cosmetics and associated areas) Editio Cantor Verlag Aulendorf, $4^{th}$ edition, 1996, pages 1498–1500] are known in the pharmaceutical industry. Depending on the area of use of the tablet, these coating compounds may be soluble in acid (solubility in the stomach), soluble in alkali (solubility in the intestine) or soluble in water. Typical representatives of these very widely used tablet coatings are the Eudragit® types manufactured by Röhm. Eudragit® L (acid-resistant) is an acid-functional polymer, while Eudragit® E (acid soluble) provides amino groups [H. P. Fiedler, Lexicon der Hilfsstoffe für Pharmazie, Kosmetik und angrenzende Gebiete (Dictionary of excipients for pharmaceutical, cosmetics and associated areas) Editio Cantor Verlag Aulendorf, 4th edition, 1996, pages 596–598]. The product Copolymer 845 manufactured by ISP, which provides tertiary amino and pyrrolidon groups, is also amino-functional, however, water soluble. Coating compounds based on cellulose derivatives (such as OPADRY® II, manufactured by Colorcon, or Sepifilm, manufactured by Seppic) are also known. Copolymers, which also contain polysaccharides, such as e.g. Surelease (by Colorcon) are also used for this purpose (see product catalogues of the individual companies).

The manufacturers provide recommendations regarding the film thickness required to achieve resistance to moisture with these coating compounds. For example, Röhm recommends film thicknesses of approximately 10 $\mu$m for the production of moisture-resistant tablet coatings; this corresponds to around one milligram of coating compound per $cm^2$ (Eudragit® product catalogue by Röhm). To achieve the recommended film thickness on the finely ground constituents of the powder in a polyelectrolyte cement (specific surface of approximately 3 $m^2$ per gram), this would have to be coated with approximately 30 grams of coating compound per gram of powder.

This represents a substantial intervention into the composition of the polyelectrolyte cement. It must be regarded as particularly important in this context that the materials named for surface coating are non-reactive additives with reference to a polyelectrolyte cement reaction. Even earlier experiments have repeatedly shown that in the case of polyelectrolyte cements, non-reactive additives generally lead to a significant deterioration of properties even in concentrations of a few percent; this applies in particular with reference to mechanical values such as compression strength or bending strength.

DE 3610844 and DE 3610845 describe surface coating agents for dental cements based on calcium aluminate. By contrast with polyelectrolyte cements, these cure through hydration rather than through chelate formation or neutralization. Since these cements cure in a basic medium, without the participation of an acid, the requirements for acid resistance of the coating agent are not comparable with the requirements placed on a polyelectrolyte cement. The polymers used for surface coating in these documents are only water soluble and are also used in concentrations up to 10% as thickeners in the aqueous reaction solution which is used for hydration.

The object of the present invention is therefore to provide a polyelectrolyte cement which can be readily produced, filled into containers and mixed, and which is so stable with regard to moisture that neither its properties nor its curing are altered within the framework of normal storage conditions. If possible, this should be achieved without the need for special packaging technology and without any reduction in the mechanical values such as compression strength and bending strength.

According to the invention, this object is resolved by a single-component or multiple-component polyelectrolyte cement and/or a granulate as described in the patent claims.

Surprisingly, by contrast with the polyelectrolyte cements known from the state of the art, a surface coating of at least a part of the metal-cation-releasing compound and/or of the polyelectrolyte allows the production of a polyelectrolyte cement which is so stable in respect of atmospheric moisture that neither its curing nor properties are changed within the context of normal storage conditions; accordingly, its usefulness is not negatively influenced and the mechanical values are comparable with those of polyelectrolyte cements known from the state of the art.

Moreover, surprisingly, the tackiness of the polyelectrolyte cement to the processing instrument is reduced and the curing transition is advantageously shortened.

Characteristic of the surface coating materials according to the invention is that these are film-forming materials which are deposited onto the surface of a solid core (reactive component of the polyelectrolyte cement), which afterwards at least partially cover this core without entering into a fixed chemical bond with this core. Within the framework of the polyelectrolyte cement reaction, the surface coating agents can preferably be separated from the core, but during storage, they protect the core from the influence of moisture.

Reactive materials, which form a chemical bond with the surface of the reactive components of the polyelectrolyte cement (e.g. silanization agents as described in DE 3941629, DE 19526224 or DE 19605272) are not surface coating agents in the sense of this invention.

Film-forming materials which are already used as coating materials in the pharmaceutical industry because of their toxicological safety (see above) are preferred. Polymeric film-forming materials, in particular those with a molar mass greater than 10,000 are particularly preferred. In this context, polymers which provide an adequately high solubility in the aqueous acidic medium so that they release the reactive component sufficiently quickly and in this manner prevent the occurrence of any significant retardation of the curing reaction are particularly preferred. Preferably, the retardation should not exceed 1 minute, particularly preferably the retardation should not exceed 30 seconds.

This requirement is in contradiction to the requirement for an effective protection from moisture. Surprisingly, it was found that per se known film-forming materials, which are used for film-coated tablets in a thickness of 40–200 $\mu$m, also fulfil this requirement, if they are applied to the reactive component of a polyelectrolyte cement in a concentration of less than 3%, preferably less than 2% and particularly preferably less than 1% (relative to the weight of the polyelectrolyte cement).

As a result of the large specific surface of the components, which is within the range 0.2 to 10, preferably 0.5 to 5, particularly preferably 1 to 3 $m^2/g$, this corresponds to a film thickness of only a few nm and is therefore smaller by a factor of 1000 to 50000 than is normal in the pharmaceutical industry. To guarantee the high level of solubility, tablet coating agents which are soluble in gastric juices are preferred; polymers containing amino-functional comonomers are particularly preferred.

These polymers can be used both as such and also in a neutralized or partially neutralized form. Any acids may be used for the neutralization. However, organic acids are preferred, and carboxylic acids are particularly preferred, in particular acids which are known to be used in polyelectrolyte cements, such as hydroxycarboxylic acids, in particular, tartaric acid or citric acid.

Surprisingly, it has been shown that significantly thinner coatings than those recommended by the pharmaceutical industry for organic coating substances used in the production of tablets are sufficient to resolve the object of the invention. Even coatings in the range 0.01 to 3 wt.-%, preferably 0.1 to 2% and very particularly preferably 0.2 to 1.5 wt.-%, lead to stable systems. Within this concentration range, the materials used for the coating are not critical with reference to the other properties of the cement. The named percentage values relate to the total weight of the surface-coated material.

Polyelectrolyte cements may be formulated as single-component or multiple-component cements. This means that the component of the polyelectrolyte cement may be provided separately packed in one or more components of the cement. This is necessary if individual reaction partners must be stored separately from one another because the reaction otherwise occurring between them would negatively influence the storage stability of the polyelectrolyte cement. For example, the three reaction partners in glass ionomer cements (GIC), the basic glass powder, the polyalkenoic acid and water, must be stored separately from one another in such a manner that no reaction occurs. Glass ionomers are therefore offered in at least two components: one component can contain the basic glass powder and the polyalkenoic acid and the second component can contain the water. The polyalkenoic acid may also be partially or completely in the water. Curing begins after the mixing of the two components. A storage stability problem regarding a reaction between these two reaction partners is probable only if the two reaction partners (a) and (b) are present at least partially in both reaction components. Then, according to the invention, it is advantageous if at least one part of the reaction partners found in the same component (a) and/or (b) is coated with an organic surface coating agent.

Water is required as a reaction partner so that curing can take place. The quantity required may very considerably depending upon the reaction partners. It is also possible for the polyelectrolyte cement according to the invention to contain no water itself, but for the water required for the reaction to originate from the surroundings, e.g. the patient's mouth. This occurs, for example, with the material class of the above-mentioned compomers. Since curing between the two reaction partners (a) and (b) does not take place without water, light-curing compomers, for instance, can also be formulated as single-component cements. In this case, the reaction between the metal-cation-releasing compound and the reaction partner (b), is, like the quantity of water (from the patient's mouth), of subordinate importance by comparison with the polymerization reaction which occurs here additionally through the addition of polymerizable compounds together with the initiators appropriate for the polymerization of these compounds.

The polyelectrolyte cements according to the invention contain 0–30 wt.-% water, preferably 0–25 wt.-% water. The compomers generally contain no water or no significant amounts of water. Glass ionomer cements modified with synthetics preferably contain 3–12 wt.-% water, particularly preferably 5–10 wt.-% water. Glass ionomer cements and polycarboxylic acid cements contain particularly preferably 5–25 wt.-% water. For example, a GIC contains 5–20 wt.-% water, preferably 8–15 wt.-% water. Unless otherwise specified, the named percentages by weight relate, in each case, to the total weight of the polyelectrolyte cement.

In the sense of the present invention, metal-cation-releasing compound should be understood to refer to all substances which are capable of releasing metal cations, which can then react with reaction partner (b) in the sense of a chelate forming reaction. In this context, the cations released should preferably be multivalent, particularly preferably divalent and trivalent. Compounds of this kind are produced for the polyelectrolyte cement in a powdered form of a particle size normal for polyelectrolyte cements [see, for example, DE-A-2061513].

Examples of metal-cation-releasing compounds are metal salts, in particular metal oxides and metal hydroxides, particularly preferably from the group of earth alkaline metals, such as, e.g. CaO, MgO, $Ca(OH)_2$, $Mg(OH)_2$, and ZnO, certain finely dispersed metals, such as finely dispersed zinc etc. (U.S. Pat. No. 3,028,247), and basic glass powders, which are particularly suitable through their proportion of divalent and trivalent ions, such as, $Ca^{2+}$, $Sr^{2+}$, $Ba^{2+}$, $La^{2+}$, $Y^{3+}$, $Al^{3+}$, in the presence of water for reaction with reaction partner (b) (see, for example, DE-A-2061513, EP-A-0023013, EP-A-02 41 277). Further examples are metal-cation-releasing silicates, such as e.g. sheet silicates, such as montmorillonites, bentonites or calcium silicates, zirconium silicates, sodium aluminium silicates, and zeoliths, including the molecular sieves.

The polyelectrolyte cement according to the invention contains the metal-cation-releasing compound preferably in a proportion of 15 to 85 wt.-%, particularly preferably 18 to 80 wt.-% and very particularly preferably 50 to 70 wt.-% relative to the total composition.

The polyelectrolyte (b) used according to the present invention is a polymer with ionically dissociable groups, which may be substituents of the polymer chain and whose number is so great that the polymers, at least in their (partially) dissociated form, are at least partially water soluble. Substituents such as —COOH, —OH, —$PO(OH)_2$, —$OPO(OH)_2$, —$SO_2(OH)$ are particularly suitable in this context. Organic polyacids (DE-A-2061513), such as polymers and copolymers of acrylic acid, methacrylic acid (EP-A-0 024 056), itaconic acid, maleic acid, citraconic acid, phosphonic acid (EP-A-0340 016; GB-A-22 91 060) are particularly preferred. Alongside these, if several polyelectrolytes are present, water-insoluble polyelectrolytes may also be present in the polyelectrolyte cement. The prerequisite is merely that at least one of the polyelectrolytes according to the above definition must be at least partially water soluble.

In the sense of the present invention, "capable of conversion into a solid state" should be understood as meaning that the polyelectrolyte is either per se a solid at room temperature or at least is a solid in its partially or completely dissociated form.

The polyelectrolytes should be able to react with the metal-cation-releasing powder component in the context of a chelate-forming reaction, preferably an acid-base reaction/neutralization reaction.

Other polyelectrolytes which are not capable of conversion into a solid state may also be present in the polyelectrolyte cement, but separately from the metal-cation-releasing compound in another component of the polyelectrolyte cement according to the invention, which will consequently be a multi-component cement.

The polyelectrolyte cement according to the invention contains the at least partially water-soluble polyelectrolytes which are capable of being converted into a solid state preferably in a proportion from 0.5 to 30 wt.-%, particularly preferably 2 to 25 wt.-% and very particularly preferably 5 to 20 wt.-%.

According to the invention, at least one part of reaction partner (a) and/or (b) is surface coated with an organic surface coating agent. The organic coating substances known in the pharmaceutical industry which are also used for the production of tablets can be used for this purpose (see above).

The surface coating can be implemented with very different materials and methods. Preferably, polymeric compounds are used. For instance, sugar solutions, polyacrylates, methacrylates, solutions based on gum arabic, gelatines, methylcellulose, other cellulose derivatives or polyethylene glycols can be used (see Ullmanns Encyklopädie der technischen Chemie, Verlag Chemie, Weinheim, 4$^{th}$ edition, 1979, pages 18–155ff; H. P. Fiedler, Lexicon der Hilfsstoffe für Pharmazie, Kosmetik und angrenzende Gebiete (Dictionary of excipients for pharmaceutical, cosmetics and associated areas) Editio Cantor Verlag Aulendorf, 4$^{th}$ edition, 1996, pages 1498–1500]. The particularly preferred organic surface coating agent is an at least partially acid-soluble surface coating agent. The very particularly preferred organic surface coating agents are the surface coating agents soluble in gastric juices including their salts. For instance, polymers with amino groups (such as Eudragit® E manufactured by Röhm), which can be used both in their amine form and also in a neutralized form, neutralized e.g. with tartaric acid (see below), are particularly suitable as coating materials. Also, polymer materials based on polysaccharides, such as OPADRY®, or based on cellulose derivatives, such as Surelease or Sepifilm, lead to equally good results.

Important representatives of these product classes are shown in the following table. These materials may serve as examples for surface coating agents in the sense of the invention.

TABLE

Film-forming agents used as surface coating agents

| Type | Film former | Molar mass | Lit. |
|---|---|---|---|
| Natural film-formers | Shellac (excretion of the Indian Lac) | Approx. 1000 | 1,2,3,4 |
| | Mastix (pistachio resin) | | 1,3 |
| | Sandarac (resin of Callitris quadrivalvis) | | 1,3 |
| | Tolubalsam (resin of Myroxylon balsamum) | | 1,3 |
| | Dammar resin (cat eye resin, resin of the dammar tree) | | 1,3 |
| | Benzoe resin (Asiatic resin) | | 1,3 |
| | Keratin (eg. from feathers) | 40,000–70,000 | 1,2,3 |
| | Maizin (Zein) (protein from maize seeds) | 10,000–22,000 | 1,3 |
| | Gum Arabic | | 2 |
| | Gelatines | | 2 |
| Semi-synthetic film-formers | Gelatines treated with formaldehyde | | 1,3 |
| | Salol (acetaldehyde-phenol-condensate) | | 1,3 |
| Cellulose derivatives | Cellulose acetate phthalate | 40,000 | 2,2a,4 |
| | Hydroxyethyl cellulose | | 2,4 |
| | Methyl cellulose | 20,000–150,000 | 4 |
| | Hydroxypropyl methyl cellulose | 10,000–150,000 | 2a,4 |
| | Hydroxypropyl cellulose | 60,000–1,200,000 | 4 |
| | Sodium-carboxymethyl cellulose | 80,000–600,000 | 4 |
| | Ethyl cellulose (e.g. Surelease-Colorcon) | | 4,7 |
| | Hydroxypropylmethyl cellulose phthalate | 20,000 | 4 |

TABLE-continued

Film-forming agents used as surface coating agents

| Type | Film former | Molar mass | Lit. |
|---|---|---|---|
| Poly(meth) acrylates | Copolymers of methacrylic esters and amino-functional methacrylates (e.g. Eudragit E - Röhm, Copolymer 845 - ISP) | 150,000 (Eudragit E) 800,000 (Eudragit E30D) | 2,4,5,6 |
| | Copolymers of (meth)acrylic acid and methymethacrylate (e.g. Eudragit L, Eudragit S, Eudragit RL, Eudragit RS-Röhm) | 135,000 (Eudragit L or S) 150,000 (Eudragit RL or RS) 250,000 (Eudragit L30D) | 2,4,5 |
| Vinyl polymers | Polyvinyl pyrrolidon | 10,000–350,000 | 2a,4 |
| | Polyvinyl acetate phthalate | 25,000–40,000 | 4 |
| Mixtures | e.g. hydroxypropyl- and hydroxypropyl-methylcellulose (e.g. Spifilm-Seppic) | | 8 |
| | e.g. hydroxypropyl cellulose and polysaccharides (e.g Opadry II - Colorcon | | 7 |

1. F. Gstirner, Grundstoffe und Verfahren der Arzneibereitung, Ferdinand Enke Verlag, Stuttgart, 1960, page 529 ff
2. P. H. List et al., Arzneformenlehre, 4$^{th}$ edition, Wissenschaftliche Verlagsgesellschaft mbH, Stuttgart, 1985, page 127 ff
2a. ibid page 540
3. Römpp Chemie Lexikon, 9$^{th}$ edition, Georg Thieme Verlag, Stuttgart, New York, 1995
4. K. H. Bauer, K.-H. Frömming, C. Führer, Pharmazeutische Technologie, 3$^{rd}$ edition, Georg Thieme Verlag, Stuttgant, New York, 1991 page 341 ff.
5. H. P. Fiedler Lexikon der Hilfsstoffe, Editio Cantor Verlag Aulendorf, 1996
6. ISP, Brochure
7. Colorcon, Brochure
8. Seppic, Brochure Since most of the surface coating agents described in the literature are only adequately soluble for the surface coating in organic solvents, the normal precautions for protection from explosions must be implemented when handling organic solvents. This can be simplified by converting the surface coating agent into a water-soluble form.

This can be achieved through conventional measures such as introducing polar or ionic groups into the surface coating agent. The neutralization of acidic or basic groups is particularly suitable in this context. For example, Eudragit® E can be converted into an adequately water-soluble Eudragit® E salt, e.g. its tartrate, for the surface coating, so that explosion precautions can be dispensed with during the surface coating because exclusively water may be used as a solvent for the surface coating.

The surface coating can be implemented in accordance with the methods described in the literature. Without limiting the invention in this context, some processes will be referred to briefly below by way of example.

Initially, the solids to be coated are mixed to a pulpy consistency with the surface coating agent dissolved in an appropriate solvent and then homogenized in an appropriate appliance with vigorous shearing. The possible mixing appliances include, for example, kneaders or various types of mixer. Finally, the surface coated material is dried and optionally sieved.

The polyelectrolyte cement may provide the usual accelerators or retarders. Examples of accelerators are short-chained, organic acids, such as acetic acid, alcohols such as ethyl alcohol, salts such as zinc acetate. Examples of retarders are organic triols such as glycerine, some organic amino alcohols such as triethanolamine (U.S. Pat. No. 3,028,247).

In the case of glass ionomer cements, the addition of chelate formers to adjust the appropriate curing process is of particular importance (DE-A-23 19 715). Numerous compounds are possible in this context, primarily those which contain the hydroxy or carboxyl groups which provide the chelate formations or both. Particularly outstanding results were achieved with tartaric acid or citric acid, in particular with a content of 5 wt.-%. The addition of a metal chelate also shows the desired effect.

In the sense of the present invention, the polyelectrolyte cements according to the invention contain 0 to 10, preferably 0 to 5 wt.-% of a compound of this kind, preferably tartaric acid.

Moreover, the curing rate can be adjusted by treating the surface of the metal-cation-releasing compound. For example, the curing rate of glass ionomer cements can be influenced by tempering the basic glass [Clinical Materials 12, 113–115 (1993)] or by the duration of the surface treatment of the basic glass with acid [DE-A-29 29 121]. Alongside this curing reaction, an additional polymerization reaction may also take place in the polyelectrolyte cement according to the invention, if polymerizable compounds and suitable initiators for the polymerization of these compounds are added.

A polymerizable compound in the above sense should be understood in this context as a compound which can enter into a polymerization reaction. Compounds of this kind may for example, carry additional substituents which can react with the metal-cation-releasing compound, such as —COOH groups. To ensure compatibility with the hydrophilic matrix formed through the curing reaction system, comprising the reaction partners (a) and (b), it is preferable if the polymerizable compounds are of a hydrophilic character. Examples of the compound capable of polymerization and/or curing used in the present context are:

(i) ethylenically-unsaturated compounds:

Vinyl, vinyl ether, acrylate, methacrylate compounds, which may also contain hydroxy groups among other groups; acrylates and methacrylates, such as methyl (meth)acrylate, n- or i-propyl(meth)acrylate, n-, i- or tert.-butyl(meth)acrylate and hydroxyalkyl(meth)acrylate, di(meth)acrylates of propandiol, butandiol, hexandiol, octandiol, nonandiol, decandiol and eicosandiol, di(meth)acrylates of ethylene glycol, diethylene glycol; esters of (meth)acrylic acid, such as triethylene glycol dimethacrylate; urethan(meth)acrylic acid; α-cyano acrylic acid; crotonic acid, cinnamic acid; sorbinic acid; (meth)acrylamides such as butyl vinyl ether; mono-N-vinyl compounds such as N-vinylpyrrolidon. Diacrylic and dimethacrylic esters of bis hydroxymethyltricyclo(5.2.1.0$^{2.6}$)-decan; 2,2-bis-b(3-methacryloxy-2-hydroxypropoxy) phenylpropane (bis-GMA); 3,6-dioxa-octamethylenedimethacrylate (TEDMA); 7,7,9-trimethyl-4,13-dioxo-3,14,-dioxa-5,12-diazahexadecan-1,16-dioxy-dimethacylate (UDMA);

(ii) Epoxides of the general formula (ii-a)

-continued in which the symbols are as follows:

Z denotes an aliphatic, cycloaliphatic or aromatic radical with 0 to 22 C-atoms or a combination of these radicals, wherein one or more C-atoms can be substituted by O, C=O, —O(C=)—, SiR$_2$ and/or NR and wherein R is an aliphatic radical with 1 to 7 C-atoms, wherein one or more C-atoms can be substituted by O, C=O and/or —(C=O)—.

A denotes an aliphatic, cycloaliphatic or aromatic radical with 1 to 18 C-atoms or a combination of these radicals, wherein one or more C-atoms can be substituted by O, C=O, —O(C=)—, SiR$_2$ and/or NR, wherein R is an aliphatic radical with 1 to 7 C-atoms, in which one or more C-atoms can be substituted by O, C=O and/or —(C=O)—.

B$_1$, B$_2$, D, E denote independently of one another a H atom or an aliphatic radical with 1 to 9 C-atoms, wherein one or more C-atoms can be substituted by O, C=O, —O(C=)—, SiR$_2$ and/or NR and wherein R is an aliphatic radical with 1 to 7 C-atoms, wherein one or more C-atoms can be substituted by O, C=O and/or —(C=O)—, n denotes 2 to 7
m denotes 1 to 10
p denotes 1 to 5
q denotes 1 to 5 and
X denotes CH$_2$, S or O;

These compounds and possibilities for their production are described in DE-A-196 48 283 or WO 95/30402.

Epoxides of the general formula (ii-b)

wherein

A, A' denote independently from one another an unbranched or branched aliphatic, cycloaliphatic or aromatic radical with 0 to 13 C-atoms or a combination of these radicals, wherein one or more C-atoms can be substituted by O, C=O, O(C=O), Si, N, S, B1, B1', B2, B2' denote independently of one another H, an unbranched or branched aliphatic, cycloaliphatic or aromatic radical with 0 to 6 C-atoms or a combination of these radicals, wherein one or more C-atoms can be substituted by O, (C=O), O(C=O), Si, N, S, F, F' denote independently of one another an unbranched or branched aliphatic, cycloaliphatic or aromatic radical with 0 to 10 C-atoms or a combination of these radicals, wherein one or more C-atoms can be substituted by O, (C=O), O(C=O), Si, N, S, D denotes an unbranched or branched aliphatic, cycloaliphatic or aromatic radical with 1 to 15 C-atoms or a combination of these radicals, wherein at least one C-atom is replaced by SiGG', SiG or Si and one or more C-atoms can be substituted by O, (C=O), O(C=O), N or S, G, G' denote independently of one another an unbranched or branched aliphatic, cycloaliphatic or aromatic radical with 0 to 8 C-atoms or a combination of these radicals, wherein one or more C-atoms can be substituted by O, (C=O), O(C=O), Si, N, S, n and m denote independently of one another 0, 1, 2 or 3 and n+m provides 2 to 6, and wherein the molar mass of the epoxide or the average molar mass of the mixture of epoxides is 250 to 1000 g/mol.

These molecules and the processes for their production are described in the German patent application (Sipox).

(iii) monomers polymerizable by ring-opening metathesis or polymers with the following structure:

wherein M is equivalent to H or a linear, branched, cyclic or polycyclic organic or metallo-organic radical. Organic radicals may be $C_1$–$C_{30}$-alkyl, $C_6$–$C_{20}$-aryl, $C_7$–$C_{30}$-alkaryl or $C_3$–$C_{30}$-cycloalkyl with 0–10 heteroatoms from the group N, O, Si, P, S and a number of n linkage points for A. Metallo-organic radicals contain, in addition to the above-named organic radicals, additional linear, branched, cyclic or polycyclic lattices of an inorganic nature.

Preferred M groups may be

----- = linkage points for A subject to the condition that Q is equal to O, S, $SO_2$ or a linear, branched or cyclic $C_1$–$C_{20}$-alkylene radical, which can also be fluorinated; m is an integer from 1–20; T is a linear, branched or cyclic saturated or unsaturated $C_1$–$C_{20}$-hydrocarbon radical and q is an integer from 3–20.

A is an unsaturated cyclic or polycyclic organic radical of the general formula wherein C is equal to H or a linear, branched or cyclic saturated or unsaturated organic $C_1$–$C_{20}$-radical with 0–10 heteroatoms from the group N, O, Si, P, S and 0–10 carbonyl groups and D is a cyclobutenyl-, cyclopentenyl radical or a radical unsaturated at the designated position and optionally additionally at another position in the ring system of the general formula in which the symbols have the following meanings:

$R^1$, $R^2$, $R^3$ denote H or a linear branched or cyclic saturated or unsaturated organic $C_1$–$C_{20}$ radicals with 0–10 heteroatoms of the group N, O, Si, P, S and 0–10 carbonyl groups, and X denotes O, NH, S or a saturated or unsaturated $C_1$–$C_{30}$ hydrocarbon radical.

The ring-opening metathesis-polymerization is also described in the literature (Comprehensive Polymer Sci.; 4; pages 109–142).

The polymerizable compounds may be contained in the polyelectrolyte cements according to the invention in proportions of 0 to 30 wt.-%, preferably 0 to 20 wt.-% and in the compomers and synthetically modified glass ionomer cements for example in proportions of 7 to 15 wt.-%.

If required, catalysts for hot, cold and/or light polymerization may be added as initiators. In this context, peroxides such as dibenzoyl peroxide, dilauryl peroxide, tert.-butyl peroctoate or tert.-butyl perbenzoate, but also α,α'azobis (isobutyroethyl ester), benzpinacol and 2.2'-dimethylbenzpinacol may be used. As photoinitiators, all substances which trigger polymerization after irradiation with UV and/or visible light may be used. These include, for example, diazonium compounds (U.S. Pat. No. 3,205,157), sulfonium compounds (U.S. Pat. No. 4,173,476) iodonium compounds (U.S. Pat. No. 4,264,703, U.S. Pat. No. 4,394,403) or bisacylphosphinoxides (EP-A-184095). Other photoinitiators are e.g. α-diketones, such as preferably 9,10-phenantrenquinone, diacetyl, furil, anisil, 4,4'-dichlorbenzil, 4,4'-dialkoxybenzil and campherquinone. Initiators for cationic light curing are e.g. the compounds described in DE-A-197 36 471. Further cationic polymerization initiators are described in DE-A-25 15 593 and in WO 96/13538. The known, radical-providing initiator systems based on peroxide/amine or peroxide/sulfituric- and/or barbituric acid, such as benzoyl or lauryl peroxide with NN-dimethyl-sym.-xylidine and NN-dimethyl-p-toluidine, are primarily suitable for cold polymerization.

Catalysts which can be added for polymerization after ring-opening metathesis are, for example, radical or cation formers and the compounds described in WO 96/23829 or the compounds described by van der Schaaf, Hafner, Mühlebach in "Angewandte Chemie" [Applied Chemistry] 1996, 108 pages 1974–1977.

Normal accelerators for the polymerization reaction, which may be added, are for, example, oxidative additives such as hydroperoxides (e.g. cumol hydroperoxide, dialkyl peroxides), peresters (e.g. tert.-butyl perbenzoate, tert.-butyl isononanoate) or inorganic oxidation agents (e.g. potassium persulfate, sodium perborate) or other radical-producing additives, such as diaryliodinium compounds, aromatic amines, alkylamines or aromatic alkylamines.

The initiators, catalysts and accelerators etc. described in the above paragraph may be contained in the polyelectrolyte cements according to the invention in proportions of 0–1 wt.-%.

Moreover, the polyelectrolyte cement according to the invention may contain excipients such as colourings, pigments, x-ray contrast agents, flow-enhancers, thixotropy agents, polymeric thickening agents or stabilizers. The normal fillers for dental materials are, for example glass and quartz powder, pyrogenic, highly dispersed silicic acids and mixtures of these components. These other additives are contained in the polyelectrolyte cements of the invention in proportions of 0–60 wt.-%.

The named fillers may also be hydrophobized, for example, by treatment with organosilanes or -siloxanes or by etherification of hydroxyl groups to alkoxy groups.

In one particular embodiment, at least one part of the components of the polyelectrolyte cement present in solid form may be presented in powdered, granulated and/or tablet form.

Granulates are understood to be sedimented accumulations of granulate grains. A granulate grain is an asymmetric aggregate or agglomerate cemented together without providing a harmonious, geometric form, made from powder or dust particles, which generally have better flow properties than powder mixtures (Ullmanns Encyklopädie der technischen Chemie, Verlag Chemie, Weinheim, $4^{th}$ edition, 1979, 18–157ff]. The surface of the grain, which may be spherical, rod-shaped or cylindrical, is uneven and ridged. [H. P. Fiedler, Lexicon der Hilfsstoffe für Pharmazie, Kosmetik und angrenzende Gebiete (Dictionary of excipients for pharmaceutical, cosmetics and associated areas) Editio Cantor Verlag Aulendorf, $4^{th}$ edition, 1996, page 722]

With reference to the practical handling of powders, granulation offers many advantages over the finely dispersed condition of products in the form of fine powders of dusts. In particular polluting the atmosphere through dust emissions, a defined flow-behaviour, simpler handling during production and packaging and also quicker dispersal or dissolution considerably improve the handling of products of this kind [Rumpf, Chemie-Ingenieur-Technik 30 and 46].

To cause finely dispersed powders to form into granulates, forces of adhesion are required between the individual grains. The adhesive forces may be derived, for example, from solid bridges such as sintering, chemical reaction, curing binding agents or through crystallization between the individual particles. Further possibilities for binding are provided by interfacial forces on freely-moving liquid surfaces, adhesion and cohesion forces, forces of attraction between solid particles and interlocking bonds.

In the pharmaceutical industry, so-called "adhesive granulation" is widespread. The granulates obtained are either used per se or are further processed to make tablets. In the context of adhesive granulation, similar compounds are used as binding agents (adhesives, granulation excipients) as are used in the production of film coatings. Alongside the compounds named in the table, the following may also be used: gelatines, starch, alginates (F. Gstirner, Grundstoffe und Verfahren der Arzneibereitung, Ferdinand Enke Verlag, Stuttgart, 1960, pages 25 ff; P.H. List et al. Arzneiformlehre, $4^{th}$ edition, Wissenschaftliche Verlagsgesellschaft mbH, Stuttgart, 1985, page 84 ff].

If the polyelectrolyte cements according to the invention are presented in the form of powder-liquid systems, mixing is often very difficult, because the powders have extremely large surface areas (see above) which make mixing very troublesome. Moreover, with the high powder-liquid ratio often required for good mechanical values, a large quantity of powder is often used with a small amount of liquid. The mixing process is made more difficult by the relatively small volume of liquid compared with the particle volume and the high specific surface of the cement which is to be wetted.

When granulation is used, the wetting of the powder with the liquid can be accelerated, because with granulation, the powder is combined internally resulting in porous structures. Through this structure, the liquid is taken up into the granulate more rapidly because of capillary forces, which considerably reduces the mixing time.

The use of granulates for dental applications has already been described in JP-06321724, JP-A-53023190, DE-A-35 11 721. DE-A-35 11 721, which describes the granulation of alginate impression compounds, describes the granulation excipients, without which granulation would not be possible. Moreover, these granulated materials are not the at least partially surface-coated material in accordance with the present invention.

Granulation excipients, which are normally used for production of the particle cluster, cannot be used in the systems according to the invention, because the quantity required for this would negatively influence the physical properties of the cured polyelectrolyte cement, in particular the curing reaction (see above).

For example, Eudragit® E is used in the pharmaceutical industry as a currently available granulation excipient because of its adhesive force. The concentrations of Eudragit® fall within a range of 5–10 wt.-%, relative to the granulate. Lower concentrations of Eudragit® do not create the desired granulates because of the limited force of adhesion, i.e. the proportion of fines would be too large to achieve the desired effect.

According to the invention, a granulate made from at least one part of the formulation constituents of the polyelectrolyte cement present in solid form is provided. In this context of an autogenous granulation, at least one part of the reaction partner (b) serves as the essential granulation agent, and the granulate breaks down again on contact with the liquid formulation constituents into the primary grain, so that the liquid and solid components of the polyelectrolyte cement can easily be mixed internally with one another by the introduction of mechanical energy.

Mechanical energy can be introduced in various ways. For example, in the case of hand mixed variants, energy is introduced via the spatula; in the case of single application capsules, energy is introduced by shaking the capsule in an automatic mixing device.

The advantages of the embodiment according to the invention include a reduced mixing time for the polyelectrolyte cements according to the invention. This leads to a shortening of the mixing time of polyelectrolyte cements packed in single application capsules in commercially available automatic mixing systems and to a significant simplification of mixing with so-called 'hand-mixing variants' of the polyelectrolyte cement according to the invention in a granular form of presentation.

Within the sense of the present invention, "autogenous granulation" should be understood to mean that the granulation takes place without the additional use of granulation excipients. On the contrary, the polyelectrolyte which is at least partially present in the powder mixture acts as a granulation excipient.

Surprisingly, two actually mutually reactive substances can be granulated in this manner, without a reaction being triggered between them. The granulate according to the invention is therefore characterized in that no significant quantities of granulation excipient are used in production and therefore that the granulate contains no significant amounts of conventional granulation agents.

The granulate is mixed with the liquid to trigger the curing reaction. Because of the very rapid absorption of water through the capillaries of the granulate, the granulate is destroyed apart from the primary grain, so that small film thicknesses are guaranteed. The liquid is absorbed leading to ease of mixing.

For dental applications, the granulate according to the invention preferably provides a mean particle size between 10 and 1000 $\mu$m particularly preferably between 50 and 500 $\mu$m.

Several known processes for producing granulates are described in the state of the art (see e.g. [Ullmanns Encyklopädie der technischen Chemie, Weinheim, 4$^{th}$ edition, 1979, 18–157 ff]). Current processes in this context are wet granulation, fusion granulation and dry granulation. These processes are essentially suitable for producing the granulate according to the invention.

Implementation of a wet granulation is particularly preferred with a solvent or a solvent mixture which partially dissolves at least a part of reaction partner (b) without triggering a reaction between the two reaction partners (a) and (b), and which is removed after granulation. Wet granulation produces particularly high levels of porosity, whereby the mixing times can be favourably reduced. The addition of solvents during granulation partially dissolves the polyacid thereby leading to the formation of the granulate. The solvent in this context must be selected in such a manner that the polyacid is partially dissolved but that no reaction is triggered. Particularly preferably, the solvents used for the wet granulation provide polar properties. Very particularly preferably, the solvent mixture used provides primarily short-chained alcohols. The granulation mixture is produced in mixers by the addition of solvents. The solvent is evaporated off after granulation.

Another preferred process for producing the granulate according to the invention is by dry granulation. In this case, the substances to be granulated are compressed to form scabs by the introduction of mechanical energy. These compressed forms are then destroyed in a grinder in a subsequent grinding stage. The resulting fragmented granulate is graded. The granules with a grain size outside the required limits are again compressed to form scabs. The granules within the required range of grain sizes are passed for packaging.

Within the context of the present invention, it has been shown that an improvement in storage stability can be achieved through granulation alone without preceding surface coating.

This affects single-component or multiple-component polyelectrolyte cements containing at least two reaction partners, (a) at least one metal-cation-releasing compound and (b) one or more polyelectrolytes which are capable of conversion into a solid state, wherein at least one of the polyelectrolytes is at least partially water soluble, wherein— in the context of an autogenous granulation—at least one part of the reaction partner (b) acts as an essential granulation excipient for the granulation of at least one part of the formulation constituents of the polyelectrolyte cement present in solid form.

The polyelectrolyte cements and granulates according to the invention can be used for the production of dental materials, in particular for the production of filling materials, fastening materials, base-filling materials, stump restructuring materials and supplementary materials (A. D. Wilson, J. W. McLean, Class Ionomer Cement, Quintessenz Verlags GmbH, Berlin 1998], endodontic materials, in particular for ortho- and retrograde filling (EP-C-04 69 573], fissure sealing materials [J. W. McLean, A. A. Wilson, Br Dent. J. 136, 269–276, 1974], orthodontic fastening materials [H. W. Seehozer, Schweiz. Monatsschr. Zahnmed. 97, 344–347, 1987] or filling materials for open furcations [C. Hüskens, C. Matter-Grütter, F. Lutz, Schweiz. Monatsschr. Zahnmed. 105, 216–221, 1995].

The polyelectrolyte cements and/or granulates of the invention are normally packed in containers such as mixing capsules, cartridges, tubes and jars. Depending on the container which is used for packaging, different instruments are used for mixing and/or application.

EXAMPLES

Surface Coating

The following exemplary embodiments describe various polyelectrolyte cements according to the invention. Example 1 (comparison) was produced by analogy with the Examples 2–10 of the invention; Example 11 (comparison) was produced by analogy with Example 12 according to the invention without the addition of an organic surface coating agent. Example 12a also serves the purpose of comparison.

All of the examples use metal-cation-releasing compounds and liquids from commercially available products (ESPE Dental AG). Ketac-Molar® powder contains a glass for glass ionomer cements and Durelon® powder contains a ZnO for polycarboxylate cements.

The coating agents were pre-dissolved in the solvents indicated in the table in order to coat the metal-cation-releasing compound. In each case, the concentration of the solvent was adjusted so that the powder was wetted optimally by the solvent. After mixing the powder in a laboratory mixer, this was dried for approximately 3 hours at approximately 100° C.

The powder was mixed, either without coating or after coating, with dry acid on the Rohn wheel for approximately 30 minutes. A copolymer made from acrylic and maleic acid (Ketac-Molar® liquid) was used in the experiments with glass ionomer cements, while the experiments with polycarboxylic cement used pure polyacrylic acid (Durelon® liquid). The type and concentration of coating agent (relative to the metal-cation-releasing compound) and the concentration of the polyalkenoic acid in the final mixture are shown in Table 1.

Figure 1:
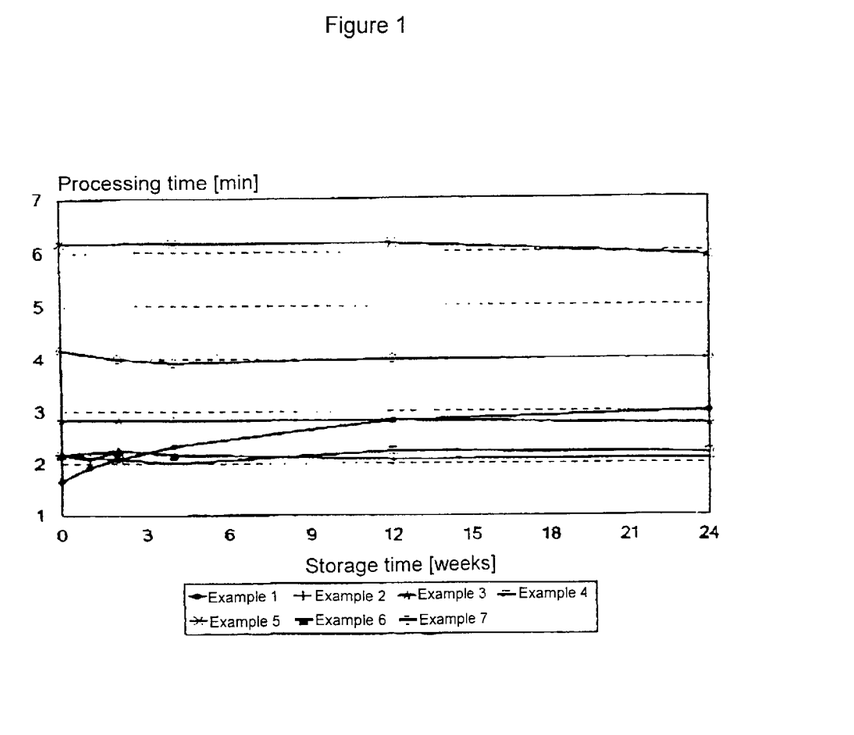
FIG. 1 a graphic representation of the processing and storage times of glass coated with Eudragit® (examples 2 to 7) by comparison with an uncoated glass (Example 1), FIG. 2 a graphic representation of the processing and storage times of glass coated with other coating agents (Examples 8 to 10) by comparison with an uncoated glass (Example 1)
Figure 2:
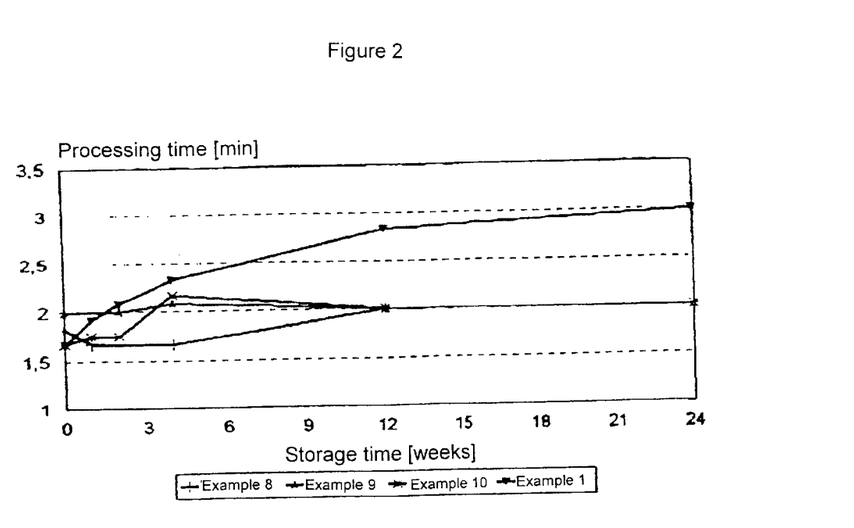
Figure 3:
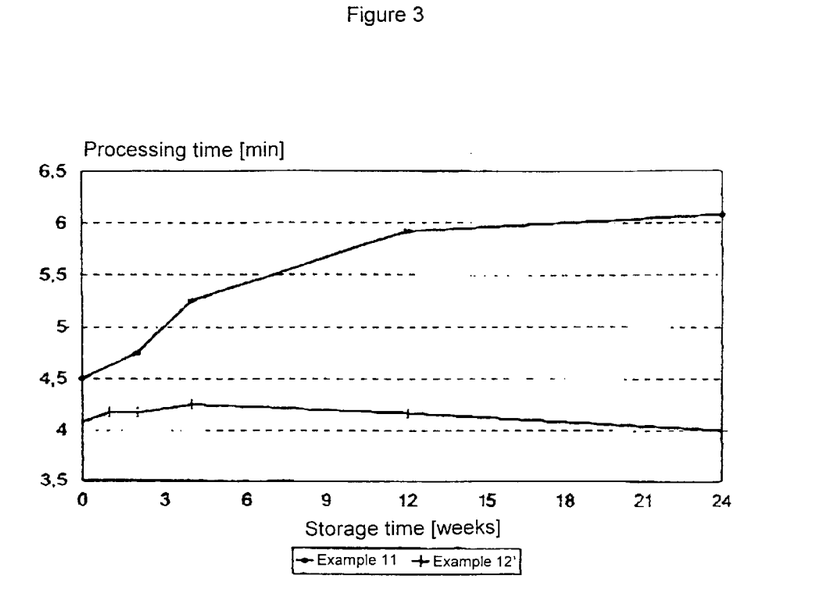
FIG. 3 a graphic representation of the processing and storage times of zinc oxide coated with Eudragit® (Example 12) by comparison with an uncoated zinc oxide (Example 11).

To measure the curing process, the two reaction partners present in solid form and homogeneously mixed—the metal-cation-releasing compound and the polyelectrolyte—were mixed in the powder/liquid (P/L) ratio indicated with the liquid shown in Table 1 and curing was measured with a rheometer of the Curometer type (Shawberry). The values shown in the table relate to the start of curring ($t_3$). Table 2 and FIGS. 1–3 represent the course of curing during storage with 50% relative humidity at 23° C.

The Eudragit® E tartrate was produced by neutralization of 45 g Eudragit® E with 11 g tartaric acid in aqueous solution.

Example 12a (Comparison)

A mixture of 95% Ketac-Molar glass powder and 5% Eudragit E tartrate was cured with Ketac-Molar liquid. Because of the strong thickening of the cement mixture, it is only possible to select a powder-liquid ratio of 2.4. The mechanical properties listed in Table 3 show a clear decline both by comparison with the reference cement and also by comparison with a cement which has been coated within the concentration range according to the invention:

bodies required for measuring the compression strength and bending strength were measured in mPa in accordance with the standard ISO 997 or in accordance with an ESPE internal standard based on ISO 4049. By way of deviation from ISO 4049 (test bodies with dimensions 15*2*2 mm) a test body with dimensions 12*2*2 mm was used.

TABLE 1

Experimental conditions

| Example no. | Metal-cation releasing compound | Coating agent Type | Conc. [%] | Solvent | Polyelectrolyte in powder mixture Type | Conc. [%] | Liquid | P/L [g/g] |
|---|---|---|---|---|---|---|---|---|
| 1 (comparison) | Ketac-Molar ® | — | 0 | — | Copolymer | 5 | Ketac-Molar ® | 3,4 |
| 2 | Ketac-Molar ® | Eudragit ® E | 0.5 | i-propanol | Copolymer | 5 | Ketac-Molar ® | 3,4 |
| 3 | Ketac-Molar ® | Eudragit ® E | 0.5 | acetone | Copolymer | 5 | Ketac-Molar ® | 3,4 |
| 4 | Ketac-Molar ® | Eudragit ® E | 0.2 | acetone | Copolymer | 5 | Ketac-Molar ® | 3,4 |
| 5 | Ketac-Molar ® | Eudragit ® E tartrate | 1.24 | water | Copolymer | 5 | Ketac-Molar ® | 3,4 |
| 6 | Ketac-Molar ® | Eudragit ® E tartrate | 0.25 | water | Copolymer | 5 | Ketac-Molar ® | 3,4 |
| 7 | Ketac-Molar ® | Eudragit ® E tartrate | 0.62 | water | Copolymer | 5 | Ketac-Molar ® | 3,4 |
| 8 | Ketac-Molar ® | Copolymer 845-ISP | 0.5 | water | Copolymer | 5 | Ketac-Molar ® | 3,2 |
| 9 | Ketac-Molar ® | OPADRY ® II Colorcon | 0.5 | water | Copolymer | 5 | Ketac-Molar ® | 3,4 |
| 10 | Ketac-Molar ® | Surelease - Colorcon | 0.5 | water | Copolymer | 5 | Ketac-Molar ® | 3,4 |
| 11 (comparison) | Durelon ® | — | 0 | — | Polyacrylic acid | 18 | Durelon ® | 3,2 |
| 12 | Durelon ® | Eudragit ® E | 0.5 | i-propanol | Polyacrylic acid | 18 | Durelon ® | 3,2 |

TABLE 2

Experimental results (start of curing $t_3$ in min:sec)

| Example no. | Starting value | Storage time [weeks] 1 | 2 | Storage time [months] 1 | 2 | 3 |
|---|---|---|---|---|---|---|
| 1 (comparison) | 1:40 | 1:55 | 2:05 | 2:20 | 2:50 | 3:00 |
| 2 | 2:10 | 2:05 | 2:15 | 2:10 | 2:05 | 2:05 |
| 3 | 2:50 | | 2:50 | 2:50 | 2:50 | 2:75 |
| 4 | 2:10 | | 2:05 | 2:00 | 2:15 | 2:12 |
| 5 | 6:10 | | | 6:10 | 6:10 | 5:55 |
| 6 | 2:10 | | 2:15 | 2:10 | | |
| 7 | 4:10 | | 4:00 | 3:55 | 4:00 | 4:00 |
| 8 | 1:50 | 1:40 | | 1:40 | 2:00 | 2:00 |
| 9 | 2:00 | | 2:00 | 2:05 | 2:00 | 2:00 |
| 10 | 1:40 | 1:45 | 1:45 | 2:10 | 2:00 | 2:00 |
| 11 (comparison) | 4:30 | | 4:45 | 5:15 | 5:55 | 6:05 |
| 12 | 4:05 | 4:10 | 4:10 | 4:15 | 4:10 | 4:00 |

The results of these experiments show that the polyelectrolyte cements according to the invention from Examples 2–10 and 12 provide an excellent storage stability within the framework of the measuring accuracy of the method (+/−15 sec), while the two comparison examples show a marked increase in the curing time even after 4 weeks, which continues during further storage.

Moreover, the following Table 3 shows, by way of example, that, for instance, in the case of Example 6 according to the invention by comparison with Example 1 (comparison), the mechanical values have not been negatively influenced by the surface coating agent. The test

TABLE 3

Compression strength and bending strength of Example 6 by comparison with Example 1 (standard deviations in brackets).

| | Compression strength [mPa] | Bending strength [mPa] |
|---|---|---|
| Example 1 (comparison) | 224 (20) | 53 (12) |
| Example 6 | 248 (21) | 56 (9) |
| Example 12a (comparison) | 147 (17) | 25 (7) |

The results from these experiments show, that an improved storage stability is achieved with the polyelectrolyte cements according to the invention without the surface coating agent exerting a negative influence on the mechanical values by comparison with a reference material which had not been surface coated.

Granulation

Example 13

An autogenously granulated powder mixture was prepared from 18 parts polyacid and 100 parts glass powder, surface coated as in Example 7, by adding 12 parts isopropanol and homogenizing in a pharmaceutical mixer for a few minutes. In order to set the required grain-size range, the moist mixture was then sieved over a sieve with a mesh size of 300 to 500 $\mu$m. The solvent was removed by subsequent drying for approximately two hours at 100° C.

Example 14 (Comparison)

Powder mixture as for Example 13 according to the invention, but surface coating and granulation were not carried out.

To test the physical properties of the polyelectrolyte cements according to standard ISO 9917 obtained in accordance with Examples 13 and 14, powder and liquid (water with 17 wt.-% tartaric acid) was mixed in a ratio of 3.8. Table 4 compares selected physical properties of the polyelectrolyte cement in accordance with Example 13 of the invention with the corresponding polyelectrolyte cements in accordance with Example 14 (comparison) and the following Example 15 (comparison).

TABLE 4

Physical properties of the polyelectrolyte cement obtained from the granulate of Example 13 according to the invention by comparison with polyelectrolyte cements obtained from Example 14 (comparison) and 15 (comparison).

|  | Example 13 | Example 14 (comparison) | Example 15 (comparison) |
|---|---|---|---|
| Compression strength [mPa] | 127 | 145 | 45 |
| Surface hardness [mPa] | 81 | 51 | 22 |
| Film thickness [$\mu$m] | 13 | 10 | 134 |

The non-granulated mixture (Example 14 (comparison)) showed signs of de-mixing during storage in the glass jar, so that the product had to be shaken before use. In this context, a considerable evolution of dust occurred so that the work surface often became contaminated with the powder on removal. Mixing the powder with the liquid was only possible with an increased input of mechanical energy.

By contrast, the granulate (Example 13 of the invention) shows no signs of de-mixing in the glass jar. The granulate does not evolve dust; it can be removed from the jar cleanly and measured very well. During mixing, it was quickly wetted and produced a very thin film. The granulated polyelectrolyte cement fulfils all requirements.

Moreover, the mixing times for powders obtainable from Example 13 and 14 (comparison) with water (water with 17 wt.-% tartaric acid) were investigated. To this end, 380 mg powder and 100 mg liquid were weighed in each case onto a mixing block. The measuring time began when the droplet of liquid came into contact with the powder and ended when a homogeneous cement without pockets of powder had been obtained. The data measured are presented in Table 5.

TABLE 5 mixing times

| Mixing experiment no. | Example 13 mixing time [sec] | Example 14 mixing time (comparison) [sec] |
|---|---|---|
| 1 | 12 | 32 |
| 2 | 11 | 35 |
| 3 | 13 | 34 |
| 4 | 10 | 28 |
| 5 | 12 | 38 |
| 6 | 10 | 32 |
| 7 | 11 | 34 |
| 8 | 14 | 29 |
| 9 | 10 | 29 |
| 10 | 10 | 34 |
| Mean value (standard deviation) | 11.3 (1.3) | 32.5 (3.0) |

The results from these experiments show that the granulates according to the invention provide clearly reduced mixing times to obtain a homogeneously mixed polyelectrolyte cement (time reduction of more than 60%). This is attributable to the considerably improved wetting of the granulates with liquid by comparison with Example 14 (comparison).

Example 15 (Comparison)

The powder mixture from Example 14 (comparison) was placed in a pharmaceutical mixer and granulated with 5% Eudragit® E relative to the granulated powder mixture. A sieve of mesh width 300 to 500 $\mu$m was used to obtain the required grain size by analogy with Example 13 of the invention. The solvent was removed again by drying at 100° C. The granulated powder was mixed as described for Example 13 and 14, and the resulting polyelectrolyte cement was tested. The data obtained are shown in Table 4.

The comparison with non-surface-treated and non-granulated powder from Example 14 (comparison) shows that even the recommended minimum amount of approx. 5% granulation excipient (see above) relative to the granulated powder mixture severely worsens the physical properties of the polyelectrolyte cement. This shows that the use of currently available granulation excipients is not appropriate for production of the granulates according to the invention.

What is claimed is:

1. A single-component or multiple-component polyelectrolyte cement comprising at least two reaction elements:
   (a) at least one metal-cation-releasing compound and
   (b) one or more polyelectrolytes capable of being converted into a solid state, wherein at least one of the polyelectrolytes is at least partially water soluble, and wherein at least a part of reaction element (a) and/or (b) is at least partially coated with an organic surface-coating agent, wherein the organic surface-coating agent is a film-forming material and is present in a quantity from 0.01 to 3 wt.-% relative to the total-weight of the surface-coated material.

2. The polyelectrolyte cement according to claim 1, wherein the two reaction elements (a) and (b) are contained at least partially within the same component of the polyelectrolyte cement.

3. The polyelectrolyte cement according to claim 1, wherein at least a part of the reaction elements (a) and/or (b) contained within the same component is coated with an organic surface-coating agent.

4. The polyelectrolyte cement according to claim 1, wherein the organic surface-coating agent is at least partially soluble in acid.

5. The polyelectrolyte cement according to claim 1, wherein at least a part of the component present in solid form is present in powdered, granulated and/or tablet form.

6. A process for production of a polyelectrolyte cement comprising the steps of:
   (a) providing at least one metal-cation-releasing compound and one or more polyelectrolytes capable of being converted into a solid state, wherein at least one of the polyelectrolytes is at least partially water soluble and acts as an essential granulation agent, and
   (b) at least partially covering a component to be granulated with the granulation agent.

7. The process according to claim 6, wherein step (b) is implemented as a wet granulation with a solvent or a solvent mixture, which dissolves at least a part of the polyelectrolytes without triggering a reaction between the metal-cationreleasing compound and polyelectrolytes, and which is removed after granulation.

8. The process according to any one of claims 6 to 7, wherein the solvents used for wet granulation provide polar properties.

9. The process according to claim 6, wherein step (b) occurs as a dry granulation.

10. A granulate obtainable through the process according to claim 6.

11. The granulate according to claim 10, which provides a mean grain size between 10 and 1000 $\mu$m.

12. A dental material comprising the polyelectrolyte cement according to any one of claims 1 to 5 and/or a granulate according to any one of claims 10 to 11.

13. A container comprising a polyelectrolyte cement according to any one of claims 1 to 5 and/or a granulate according to any one of claims 10 to 11.

14. An application device comprising a polyelectrolyte cement according to any one of claims 1 to 5 and/or a granulate according to any one of claims 10 to 11.

* * * * *

UNITED STATES PATENT AND TRADEMARK OFFICE
CERTIFICATE OF CORRECTION

PATENT NO. : 6,719,834 B1
DATED : April 13, 2004
INVENTOR(S) : Braun, Peter

It is certified that error appears in the above-identified patent and that said Letters Patent is hereby corrected as shown below:

Title page,
Item [56], References Cited, U.S. PATENT DOCUMENTS, delete "5,512,611    A" and insert -- 5,512,611 --, therefor.

Column 7,
Line 48, delete "eg." and insert -- e.g. --, therefor.

Column 8,
Line 12, delete "methymethacrylate" and insert -- methylmethacrylate --, therefor.
Line 22, delete "e.g" and insert -- e.g. --, therefor.
Line 31, delete ""stuttgant" and insert -- Stuttgart --, therefor.

Column 16,
Line 55, delete "curring" and insert -- curing --, therefor.

Column 20,
Line 39, delete "total-weight" and insert -- total weight --, therefor.

Signed and Sealed this

Fifteenth Day of November, 2005

JON W. DUDAS
*Director of the United States Patent and Trademark Office*